(12) United States Patent
Leyva et al.

(10) Patent No.: US 11,993,522 B2
(45) Date of Patent: May 28, 2024

(54) TECHNOLOGIES FOR SANITIZING RESERVOIRS

(71) Applicant: SoClean, Inc., Peterborough, NH (US)

(72) Inventors: Timothy Leyva, Bellingham, MA (US); William E. Olszta, Webster, MA (US)

(73) Assignee: SOCLEAN, INC., Peterborough, NH (US)

( * ) Notice: Subject to any disclaimer, the term of this patent is extended or adjusted under 35 U.S.C. 154(b) by 1196 days.

(21) Appl. No.: 16/587,306

(22) Filed: Sep. 30, 2019

(65) Prior Publication Data

US 2020/0024167 A1 Jan. 23, 2020

Related U.S. Application Data (63) Continuation of application No. 15/499,456, filed on Apr. 27, 2017, now Pat. No. 10,427,961, which is a
(Continued)

(51) Int. Cl.
*A61L 2/20* (2006.01)
*A61L 2/18* (2006.01)
(Continued)

(52) U.S. Cl.
CPC ............ *C02F 1/78* (2013.01); *A61L 2/183* (2013.01); *A61L 2/202* (2013.01); *A61L 2/24* (2013.01); *A61M 16/00* (2013.01); *A61M 16/06* (2013.01); *A61M 16/0816* (2013.01); *A61M 16/0875* (2013.01); *A61M 16/1095* (2014.02); *A61M 16/16* (2013.01); *C02F 1/283* (2013.01); *A61L 2202/11* (2013.01); *A61L 2202/14* (2013.01); *A61L 2202/24* (2013.01);
(Continued)

(58) Field of Classification Search
CPC ...................................................... A61L 2/202
See application file for complete search history.

(56) References Cited

U.S. PATENT DOCUMENTS 4,019,986 A * 4/1977 Burris ...................... C02F 1/78
 210/220
4,035,657 A 7/1977 Carlson
(Continued)

FOREIGN PATENT DOCUMENTS

CN 1377708 11/2002
CN 2710637 7/2005
(Continued)

OTHER PUBLICATIONS

Office Action dated Feb. 3, 2020, issued in U.S. Appl. No. 16/190,996, 9 pages.
(Continued)

*Primary Examiner* — Donald R Spamer
(74) *Attorney, Agent, or Firm* — Grossman, Tucker, Perreault & Pfleger, PLLC (57) ABSTRACT

Technologies (e.g., devices, systems and methods) for sanitizing reservoirs are described. In some embodiments, the technologies include a sanitization gas system and a connector unit or a hole in the reservoir wall, configured to connect a supply line to the reservoir. The connector unit may include an inlet passageway for supplying sanitizing gas (e.g., ozone) into the reservoir.

13 Claims, 4 Drawing Sheets

Related U.S. Application Data continuation-in-part of application No. 15/441,929, filed on Feb. 24, 2017, now Pat. No. 10,398,797, which is a continuation of application No. 15/142,111, filed on Apr. 29, 2016, now Pat. No. 9,610,373, said application No. 15/499,456 is a continuation-in-part of application No. 15/141,216, filed on Apr. 28, 2016, now Pat. No. 9,669,124, which is a continuation-in-part of application No. PCT/US2015/029418, filed on May 6, 2015, said application No. 15/142,111 is a continuation of application No. 14/232,773, filed as application No. PCT/US2012/046593 on Jul. 13, 2012, now Pat. No. 9,358,316.

(60) Provisional application No. 61/508,341, filed on Jul. 15, 2011.

(51) Int. Cl.
| | |
|---|---|
| *A61L 2/24* | (2006.01) |
| *A61M 16/00* | (2006.01) |
| *A61M 16/06* | (2006.01) |
| *A61M 16/08* | (2006.01) |
| *A61M 16/10* | (2006.01) |
| *A61M 16/16* | (2006.01) |
| *C02F 1/28* | (2023.01) |
| *C02F 1/78* | (2023.01) |
| *A61M 16/20* | (2006.01) |

(52) U.S. Cl.
CPC ... *A61M 16/208* (2013.01); *A61M 2202/0216* (2013.01); *A61M 2205/27* (2013.01); *A61M 2209/10* (2013.01); *C02F 2201/782* (2013.01); *C02F 2303/04* (2013.01)

(56) References Cited

U.S. PATENT DOCUMENTS

| | | |
|---|---|---|
| 4,110,419 A | 8/1978 | Miller |
| 4,207,291 A | 6/1980 | Byrd et al. |
| 4,465,522 A | 8/1984 | Taldo et al. |
| 4,517,159 A | 5/1985 | Karlson |
| D295,074 S | 4/1988 | Jerge et al. |
| 4,743,275 A | 5/1988 | Flanagan |
| 4,787,980 A | 11/1988 | Ackermann et al. |
| 5,029,879 A | 7/1991 | Strang, Sr. et al. |
| 5,120,512 A | 6/1992 | Masuda |
| 5,207,237 A * | 5/1993 | Langford ............... A61L 2/202 134/102.1 |
| 5,344,622 A | 9/1994 | Faddis et al. |
| 5,508,006 A | 4/1996 | Gabele et al. |
| 5,520,893 A | 5/1996 | Kasting, Jr. et al. |
| D371,203 S | 6/1996 | Deeds |
| D390,645 S | 2/1998 | Hanrahan et al. |
| 5,761,069 A | 6/1998 | Weber et al. |
| 5,920,075 A | 7/1999 | Whitehead |
| 6,024,066 A | 2/2000 | Nakayama et al. |
| 6,134,806 A | 10/2000 | Dhaemers |
| 6,158,784 A | 12/2000 | Lavender |
| 6,276,304 B1 | 8/2001 | Tai |
| 6,280,633 B1 | 8/2001 | Conrad et al. |
| 6,365,601 B1 | 4/2002 | Fournier |
| 6,379,617 B1 | 4/2002 | Spickermann |
| 6,379,632 B1 | 4/2002 | Kinoshita et al. |
| D476,423 S | 6/2003 | Picot et al. |
| 6,576,190 B1 | 6/2003 | Park |
| 6,605,260 B1 | 8/2003 | Busted |
| D487,315 S | 3/2004 | Picot et al. |
| 6,752,151 B2 | 6/2004 | Hill |
| 7,022,225 B1 | 4/2006 | Clawson et al. |
| 7,491,321 B1 | 2/2009 | Maas et al. |
| 7,520,910 B2 | 4/2009 | Tilley |
| 7,527,603 B2 | 5/2009 | An |
| 7,676,276 B2 | 3/2010 | Karell |
| 7,767,168 B2 | 8/2010 | Namespetra et al. |
| 7,794,522 B2 | 9/2010 | Bliss et al. |
| 7,845,350 B1 | 12/2010 | Kayyali et al. |
| 8,051,853 B2 | 11/2011 | Berthon-Jones |
| 8,146,946 B1 | 4/2012 | Emond |
| 8,176,771 B2 | 5/2012 | Onishi et al. |
| 8,215,465 B2 | 7/2012 | Iceberg |
| 8,431,076 B2 | 4/2013 | Fraundorfer |
| D692,155 S | 10/2013 | Matoba et al. |
| 8,770,198 B2 | 7/2014 | Yee |
| 8,815,164 B1 | 8/2014 | Al Azemi |
| D719,673 S | 12/2014 | Leyva et al. |
| D719,674 S | 12/2014 | Leyva et al. |
| 8,915,380 B2 | 12/2014 | Sowerby et al. |
| 9,022,247 B2 | 5/2015 | Enigmann |
| D733,315 S | 6/2015 | Lui |
| D733,316 S | 6/2015 | Lui |
| D748,280 S | 1/2016 | Lui |
| 9,358,311 B2 | 6/2016 | Leyva |
| 9,358,316 B2 | 6/2016 | Leyva |
| D761,142 S | 7/2016 | Golta et al. |
| 9,402,928 B2 | 8/2016 | Tremblay |
| D776,290 S | 1/2017 | Wan et al. |
| 9,610,373 B2 | 4/2017 | Leyva |
| 9,616,147 B2 | 4/2017 | Leyva |
| 9,669,124 B2 | 6/2017 | Leyva et al. |
| D802,788 S | 11/2017 | Cormier et al. |
| 9,895,461 B2 | 2/2018 | Leyva et al. |
| 9,907,872 B2 | 3/2018 | Schmidt et al. |
| D819,190 S | 5/2018 | Cormier et al. |
| 10,052,397 B2 | 8/2018 | Leyva |
| 10,232,072 B2 | 3/2019 | Leyva et al. |
| 10,264,913 B2 | 4/2019 | Leyva |
| 10,398,797 B2 | 9/2019 | Leyva |
| 10,427,961 B2 | 10/2019 | Leyva et al. |
| 10,434,204 B2 | 10/2019 | Leyva et al. |
| 10,434,205 B2 | 10/2019 | Leyva |
| 10,456,492 B2 | 10/2019 | Leyva |
| 10,485,888 B2 | 11/2019 | Schmidt et al. |
| 10,842,897 B2 | 11/2020 | Schwartz |
| 10,980,905 B2 | 4/2021 | Bohman |
| 11,000,611 B1 | 5/2021 | He |
| 2002/0139124 A1 | 10/2002 | Palermo |
| 2003/0000966 A1 | 1/2003 | Shelton |
| 2003/0063997 A1 | 4/2003 | Fryer et al. |
| 2003/0065292 A1 | 4/2003 | Darouiche et al. |
| 2003/0065297 A1 | 4/2003 | Davis et al. |
| 2003/0071069 A1 * | 4/2003 | Shelton ............... C02F 1/78 222/190 |
| 2004/0007000 A1 | 1/2004 | Takeda |
| 2004/0251125 A1 | 12/2004 | Yu |
| 2005/0017380 A1 | 1/2005 | Namespetra et al. |
| 2005/0019237 A1 | 1/2005 | Riley |
| 2005/0168907 A1 | 8/2005 | Sekoguchi |
| 2005/0186108 A1 | 8/2005 | Fields |
| 2005/0220665 A1 | 10/2005 | Ding |
| 2006/0130834 A1 | 6/2006 | Chen |
| 2006/0272682 A1 | 12/2006 | Langford |
| 2007/0031778 A1 | 2/2007 | Helfenbein et al. |
| 2007/0065335 A1 | 3/2007 | Bedard et al. |
| 2008/0050290 A1 | 2/2008 | Yui |
| 2008/0118411 A1 | 5/2008 | D'Arinzo |
| 2009/0080809 A1 | 3/2009 | Pham |
| 2009/0267242 A1 * | 10/2009 | Nichols ............... A61M 11/007 261/151 |
| 2010/0047116 A1 | 2/2010 | Garner |
| 2010/0111792 A1 | 5/2010 | Nelson |
| 2010/0112677 A1 | 5/2010 | Onishi et al. |
| 2010/0147302 A1 | 6/2010 | Selvarajan et al. |
| 2011/0031081 A1 | 2/2011 | Iceberg |
| 2012/0164025 A1 | 6/2012 | Stockley, III et al. |
| 2012/0227745 A1 | 9/2012 | Arcilla et al. |
| 2013/0177475 A1 | 7/2013 | Finch |
| 2013/0239994 A1 | 9/2013 | Przyjemski |
| 2014/0112837 A1 | 4/2014 | Huang |
| 2014/0154134 A1 | 6/2014 | Leyva |
| 2015/0004061 A1 | 1/2015 | Kain et al. |
| 2016/0235875 A1 | 8/2016 | Schmidt et al. |

(56) References Cited

U.S. PATENT DOCUMENTS

| | | |
|---|---|---|
| 2017/0165443 A1 | 6/2017 | Leyva |
| 2017/0202990 A1 | 7/2017 | Leyva |
| 2017/0209610 A1 | 7/2017 | Leyva et al. |
| 2017/0224857 A1 | 8/2017 | Leyva et al. |
| 2017/0225985 A1 | 8/2017 | Leyva et al. |
| 2017/0370013 A1 | 12/2017 | Bahar |
| 2018/0028770 A1 | 2/2018 | Parrish |
| 2018/0161466 A1 | 6/2018 | Schmidt et al. |
| 2018/0207307 A1 | 7/2018 | Schwartz |
| 2018/0264157 A1 | 9/2018 | Benedek |
| 2018/0311391 A1 | 11/2018 | Leyva |
| 2018/0311595 A1 | 11/2018 | Leyva |
| 2019/0076561 A1 | 3/2019 | Leyva et al. |
| 2019/0076562 A1 | 3/2019 | Schmidt et al. |
| 2019/0083668 A1 | 3/2019 | Schmidt et al. |
| 2019/0151487 A1 | 5/2019 | Leyva |
| 2019/0167828 A1 | 6/2019 | Leyva |
| 2019/0336627 A1 | 11/2019 | Lucio |
| 2019/0388575 A1 | 12/2019 | Leyva et al. |
| 2020/0000950 A1 | 1/2020 | Bohman |
| 2020/0024167 A1 | 1/2020 | Leyva et al. |
| 2020/0069362 A1 | 3/2020 | Paesch |

FOREIGN PATENT DOCUMENTS

| | | |
|---|---|---|
| CN | 1951507 | 4/2007 |
| CN | 2905066 | 5/2007 |
| CN | 201156965 | 12/2008 |
| CN | 105031693 | 11/2015 |
| CN | 108671253 | 10/2018 |
| EP | 2731632 | 8/2017 |
| JP | S62230601 | 10/1987 |
| JP | H0724064 | 1/1995 |
| JP | 200288091 | 10/2000 |
| JP | 2005270589 | 10/2005 |
| KR | 1020040098412 | 11/2004 |
| KR | 101839063 | 3/2018 |
| WO | 03068274 | 8/2003 |
| WO | 2008116165 | 9/2008 |
| WO | 2011058472 | 5/2011 |
| WO | 2013012696 | 1/2013 |
| WO | 2015171730 | 11/2015 |
| WO | 2017189915 | 11/2017 |
| WO | 2017189916 | 11/2017 |
| WO | 2018200525 | 11/2018 |

OTHER PUBLICATIONS

Office Action dated Feb. 18, 2020, issued in Canadian Patent Application No. 3,005,981, 3 pages.
Office Action dated Mar. 19, 2020, issued in Korean Patent Application No. 10-2020-7003298, 4 pages.
Office Action dated Mar. 23, 2020, issued in Chinese Patent Application No. 201710179049.1, 8 pages.
Office Action dated Apr. 7, 2020, issued in U.S. Appl. No. 16/780,492, 13 pages.
Office Action dated Apr. 13, 2020, issued in U.S. Appl. No. 16/782,892, 15 pages.
Office Action dated Apr. 15, 2020, issued in U.S. Appl. No. 15/444,916, 16 pages.
Office Action dated Apr. 23, 2020, issued in U.S. Appl. No. 16/780,355, 14 pages.
Notice of Allowance dated Apr. 28, 2020, issued in U.S. Appl. No. 16/780,492, 7 pages.
ResMed VPAP III ST-A with QuickNav Clinical Guide, copyright 2008 ("ResMed Guide"). Cited by opposing counsel in connection with *SoClean Inc. v. Sunset Healthcare Solutions, Inc.*, Civil action No. 1:20-cv-10351-IT (U.S. Dist. Ct. Massachusetts).
VPAP IV and VPAP IV ST Product Training ("ResMed Presentation"). Cited by opposing counsel in connection with *SoClean Inc. v. Sunset Healthcare Solutions, Inc.*, Civil action No. 1:20-cv-10351-IT (U.S. Dist. Ct. Massachusetts). Publication Date is unknown to Applicant, but was asserted by opposing counsel in the noted litigation to be in 2008.
Ozone MSDS (Material Safety Data Sheets), Ozone Solutions, Jun. 1, 2000, http://www.ozoneapplications.com/info/ozone_msds.htm, 5 pages.
CPAP Guardian TB-316, America Tyson Industrial Group (Asia Pacific) Limited, http://www.ecvv.com/products/2314441.html, Nov. 91, 2009, downloaded from Internet Jul. 8, 2016, 3 pages.
International Search Report and Written Opinion dated Sep. 17, 2012, issued in PCT Application No. PCT/US12/46593, 6 pages.
International Search Report and Written Opinion dated Jul. 24, 2015, issued in PCT Application No. PCT/US15/29418, 9 pages.
U.S. Office Action dated Jun. 30, 2016, issued in U.S. Appl. No. 15/141,216, 13 pages.
U.S. Office Action dated Jul. 13, 2016, issued in U.S. Appl. No. 15/142,060, 18 pages.
U.S. Office Action dated Jul. 14, 2016, issued in U.S. Appl. No. 15/142,111, 10 pages.
U.S. Office Action dated Jul. 28, 2016, issued in U.S. Appl. No. 15/142,085, 15 pages.
U.S. Office Action dated Oct. 6, 2016, issued in U.S. Appl. No. 15/141,152, 11 pages.
U.S. Office Action dated Nov. 23, 2016, issued in U.S. Appl. No. 15/141,216, 9 pages.
U.S. Office Action dated Nov. 23, 2016, issued in U.S. Appl. No. 15/142,085, 8 pages.
U.S. Office Action dated Feb. 23, 2017, issued in U.S. Appl. No. 29/562,755, 8 pages.
U.S. Office Action dated Feb. 27, 2017, issued in U.S. Appl. No. 29/562,756, 7 pages.
U.S. Office Action dated Mar. 17, 2017, issued in U.S. Appl. No. 15/141,152, 14 pages.
Office Action dated Sep. 21, 2017, issued in U.S. Appl. No. 15/142,085, 9 pages.
Notice of Allowance dated Oct. 13, 2017, issued in U.S. Appl. No. 15/481,919, 7 pages.
U.S. Final Office Action dated Feb. 5, 2018, issued in U.S. Appl. No. 15/141,152, 16 pages.
U.S. Office Action dated Apr. 3, 2018, issued in U.S. Appl. No. 15/873,506, 7 pages.
U.S. Notice of Allowance dated Apr. 27, 2018, issued in U.S. Appl. No. 15/142,085, 8 pages.
International Search Report and Written Opinion dated Jul. 13, 2018, issued in PCT International Patent Application No. PCT/US18/29140, 12 pages.
Office Action dated Aug. 9, 2018, issued in Japanese Patent Application No. 2014-520352, 5 pages. English language translation provided.
Office Action dated Sep. 5, 2018, issued in Chinese Patent Application No. 2016105175158, 10 pages. English language translation provided.
Office Action dated Sep. 17, 2018, issued in U.S. Appl. No. 15/441,929, 10 pages.
Examination Report dated Sep. 26, 2018, issued in Australian Patent Application No. 2017228723, 6 pages.
Preliminary Report on Patentability dated Nov. 8, 2018, issued in PCT International Patent Application No. PCT/US2017/029950, 9 pages.
Office Action dated Jan. 16, 2019, issued in Korean Patent Application No. 10-2018-7009274, 5 pages. English language translation provided.
Notice of Allowance dated Jan. 18, 2019, issued in U.S. Appl. No. 15/441,929, 7 pages.
Office Action dated Jan. 22, 2019, issued in U.S. Appl. No. 16/190,996, 10 pages.
Office Action dated Mar. 4, 2019, issued in U.S. Appl. No. 15/444,916, 16 pages.
Office Action dated Mar. 4, 2019, issued in U.S. Appl. No. 16/257,898, 13 pages.
Office Action dated Mar. 14, 2019, issued in U.S. Appl. No. 16/270,141, 12 pages.
U.S. Appl. No. 16/257,898, filed Jan. 25, 2019.

(56) References Cited

OTHER PUBLICATIONS

Examination Report dated Jun. 7, 2019, issued in Canadian Patent Application No. 3,005,981, 3 pages.
Preliminary Report on Patentability dated Nov. 7, 2019, issued in PCT Patent Application No. PCT/US2018/029140, 11 pages.
Notice of Allowance dated Nov. 15, 2019, issued in Australian Patent Application No. 2018200514, 4 pages.
Extended Search Report dated Nov. 29, 2019, issued in European Patent Application No. 17790471.1, 9 pages.
Examination Report dated Jan. 13, 2020, issued in Chilean Patent Application No. 201803063, 17 pages. English language machine translation included.
Examination Report dated May 15, 2019, issued in Australian Patent Application No. 2017228723, 5 pages.
Notice of Allowance dated May 17, 2019, issued in U.S. Appl. No. 16/270,141, 7 pages.
Notice of Allowability dated May 22, 2019, issued in U.S. Appl. No. 15/499,456, 5 pages.
Notice of Allowance dated May 28, 2019, issued in U.S. Appl. No. 15/499,378, 7 pages.
Notice of Allowance dated Jun. 20, 2019, issued in U.S. Appl. No. 16/257,898, 8 pages.
U.S. Office Action dated Jul. 26, 2019, issued in U.S. Appl. No. 16/190,996, 12 pages.
Lenntech "Ozone Generation", Wayback Machine Capture, Mar. 28, 2010, (Year 2010), 3 pages.
Office Action dated Apr. 28, 2019, issued in Chinese Patent Application No. 2017101790491, 10 pages.
Office Action dated Jul. 29, 2019, issued in Chinese Patent Application No. 2017101786091, 10 pages.
Office Action dated Jul. 29, 2019, issued in Chinese Patent Application No. 2017101790472, 8 pages.
Office Action dated Aug. 6, 2019, issued in Chinese Patent Application No. 2017101795495, 9 pages.
Notice of Allowance dated Aug. 8, 2019, issued in U.S. Appl. No. 15/141,152, 8 pages.
Examination Report dated Aug. 13, 2019, issued in Australian Patent Application No. 2018200514, 6 pages.
Notice of Acceptance dated Aug. 14, 2019, issued in Australian Patent Application No. 2017228723, 4 pages.
Office Action dated Sep. 17, 2019, issued in U.S. Appl. No. 15/444,916, 17 pages.
Notice of Allowance dated Oct. 8, 2019, issued in Japanese Application No. 2017-149891, 4 pages.
Preliminary Report on Patentability dated Nov. 8, 2018, issued in PCT International Patent Application No. PCT/US2017/029949, 9 pages.
Chaunet et al., "The Sterilization Technology for the 21st Century", TS03, Inc. Québec, Canada, 2007.
Office Action dated Oct. 20, 2021 in U.S. Appl. No. 17/025,634. 9 pages.
Goodknight 420G Patient Manual, 2005, Nellcor Puritan Bennett Inc., pp. i-vi; pp. 1-23.
Office Action dated May 10, 2021, issued in Indian Patent Application No. 201827043772, 8 pages.
SoClean 2 PAP Disinfecting Device User Guide Copyright 2011-2014, Inceptus, Inc.
Ohkawa et al. "High grade disinfection using high-density ozone," J Adv Oxid Tech, 7, 154-160, (2004).
International Search Report and Written Opinion dated Aug. 16, 2017, issued in PCT Patent Application No. PCT/US17/29950, 11 pages.
U.S. Office Action dated Aug. 3, 2017, issued in U.S. Appl. No. 15/141,152, 14 pages.
International Search Report and Written Opinion dated Aug. 2, 2017, issued in PCT Patent Application No. PCT/US17/29949, 11 pages.
U.S. Office Action dated Jun. 13, 2017, issued in U.S. Appl. No. 15/481,919, 10 pages.
Keep your CPAP machine clean and safe, Oct. 18, 2010—Available at https://www.cpap.co.uk/2010/10/keep-your-cpap-machine-clean-and-safe.
GoodKnight H20 Heated Humidifier User's Manual, 2006 Nellcor Puritan Bennett Inc., pp. i-iv and 1-16.
Hoffrichter Trend II User's Manual (date unknown), Germany, pp. 1-79.
Hudson RCI Product Catalog (2004-2005).
KnightStar(R) 330 User's Manual, 2006, Nellcor Puritan Bennett, 68 pages.
DeVilbiss® DV54 AutoAdjust CPAP Series (DeVilbiss® SleepCube Positive Airway Pressure Device) User Manual (2009). Available at https://www.manualslib.com/manual/1577762/Devilbiss-Intellipap-Dv54.html, pp. 1-183.
Sunset Healthcare Solutions, Inc's Preliminary Patent Disclosures Pursuant to Local Rule 16.6(d)(4) in *SoClean, Inc. v. Sunset Healthcare Solutions, Inc,* in Civil Action No. 1:20-cv-10351-IT.
Sunset Healthcare Solutions, Inc's Second Amended Counterclaims in *SoClean, Inc. v. Sunset Healthcare Solutions, Inc,* in Civil Action No. 1:20-cv-10351-IT and Consolidated Case No. 1:21-cv-1013IT.
Memorandum in Support of SoClean's Motion to Dismiss Counts Eight and Nine of Sunset's Second Amended Counterclaims, *SoClean, Inc. v. Sunset Healthcare Solutions, Inc,* in Civil Action No. 1:20-cv-10351-IT and Consolidated Case No. 1:21-cv-1013IT.
Defendant Sunset's Memorandum in Opposition to SoClean's Motion to Dismiss Counts Eight and Nine of Sunset's Second Amended Counterclaims. C.A. No. 1:20-cv-10351-IT. Filed Jul. 23, 2021, 165 pages.
9055 Series DeVilbiss RPM Bilevel CPAP System Instruction Manual, 66 pages.
Al Ashry, et al. "Humidification during Mechanical Ventilation in the Adult Patient", vol. 2014, Article ID 715434, Hindawi Publishing Corporation, BioMed Research International. 12 pages.
Murphy, "Ozone—The Latest Advance in Sterilization of Medical Developments", Canadian Operating Room Nursing Journal, vol. 24, No. 2, Jun. 2006, pp. 28, 30-32, 37 and 38.
Ishizaki, et al., "Inactivation of Bacillus Spores by Gaseous Ozone", Journal of Applied Bacteriology, 1986, 60, 67-72.
Tornado, New Kind of CPAP Guardian, User Manual, Sunset, 8 pages.
Office Action dated Apr. 28, 2021 in JP 2019-201674, 3 pages.
First Examination Report issued in Indian Patent Application No. 60/MUMNP/2014, dated Jul. 10, 2019, 6 pages.
Office Action dated Nov. 18, 2020 in CN 201780025983.6.
Office Action dated May 18, 2021 in CN 201780025983.6. 8 pages.
Office Action dated Nov. 1, 2020 in KR 10-2020-7026960. 3 pages.
Office Action dated Jul. 26, 2021, issued in Chinese Patent Application No. 2017101790472, 4 pages.
Office Action dated May 29, 2020, issued in Chinese Patent Application No. 2017101795495, 4 pages.
Office Action dated Jul. 1, 2020, issued in Chinese Patent Application No. 2017101790472.
Office Action dated Jul. 3, 2020, issued in Chinese Patent Application No. 2017101786388, 8 pages.
Restriction Requirement issued in related U.S. Appl. No. 17/025,634, dated Aug. 2, 2021 (6 pages).
Office Action dated May 11, 2021 in BR112018-071444-5.
China Office Action from related matter CN201780025983.6 dated May 9, 2020. English translation attached.
China Office Action from related matter CN201710179459.5 dated May 29, 2020, English translation attached.
International Search Report and Written Opinion from related matter PCT/US20/23631 dated Jun. 3, 2020. 13 pages.
China Office Action from related application CN 201710186091 dated Jul. 1, 2020, English translation attached.
China Office Action from related application CN 20171017904.2 dated Jul. 1, 2020, English translation attached.
U.S. Office Action from related matter U.S. Appl. No. 16/191,059 dated Jun. 11, 2020. 11 pages.
U.S. Final Office Action from related matter U.S. Appl. No. 16/294,097 dated Jun. 11, 2020. 13 pages.
U.S. Office Action from related matter U.S. Appl. No. 15/880,962 dated Jun. 11, 2020. 13 pages.

(56) References Cited

OTHER PUBLICATIONS

Office Action dated Jul. 29, 2019, issued in Chinese Patent Application No. 2017101786091. 15 pages. English translation attached.
Final Office Action dated Feb. 4, 2019, issued in U.S. Appl. No. 15/141,152, 14 pages.
Examination Report dated Feb. 15, 2019, issued in Australian Patent Application No. 2018200514, 5 pages.
Notice of Allowance dated Apr. 30, 2019, issued in U.S. Appl. No. 15/441,929, 5 pages.
Office Action dated Mar. 4, 2019, issued in U.S. Appl. No. 16/257,898.
Office Action dated Mar. 14, 2019, issued in U.S. Appl. No. 16/270,141.
Notice of Allowance dated Mar. 19, 2019, issued in U.S. Appl. No. 15/499,456, 12 pages.
Extended European Search Report from related Application No. 20773414.6 dated Nov. 17, 2022. 4 pages.
Office Action dated Apr. 2, 2019, issued in Japanese Patent Application No. 2017-0149891, 7 pages.
Office Action dated Oct. 30, 2018, issued in U.S. Appl. No. 15/499,456, 13 pages.
Notice of Allowance dated Oct. 31, 2018, issued in U.S. Appl. No. 15/873,506, 8 pages.
Office Action amendment dated Oct. 31, 2018, issued in U.S. Appl. No. 15/499,456, 13 pages.
Office Action dated Nov. 6, 2018, issued in U.S. Appl. No. 15/499,378, 18 pages.

\* cited by examiner

TECHNOLOGIES FOR SANITIZING RESERVOIRS

FIELD

The present disclosure generally relates to systems and devices for sanitizing reservoirs with a sanitizing gas. Methods of sanitizing reservoirs are also disclosed.

BACKGROUND

A wide variety of devices include reservoirs for holding water and/or another liquid. Depending on the device, water may be drawn from the reservoir for various end uses. For example, many coffee makers include a water reservoir that holds water that is used to make coffee on demand. Medical devices such as continuous positive airway pressure devices, ventilators, and the like may also include one or more water reservoirs, e.g., for humidifying air administered to a patient. Humidifiers may also include a reservoir for the purpose of holding water that is used to humidify air.

Bacteria, mold, viruses and/or other contaminants may grow or otherwise accumulate within a reservoir, particularly if the reservoir is infrequently cleaned and/or water therein is allowed to remain stagnant for long periods (e.g. days) before it is replaced or replenished with fresh water. Despite this risk, users of devices that include a reservoir often do not clean the reservoir or replenish the reservoir with fresh water when the water therein has been sitting for a long period of time.

The foregoing issues are compounded by the fact that many commonly recommended methods for the reservoir of a device can be messy, time consuming, and inconvenient. For example, the user guide of some devices with reservoirs may recommend cleaning the reservoir and/or other components of the machine using a cleaning solution that is a mixture of water and vinegar. Such methods can be inconvenient, as they often require the user to prepare the cleaning solution themselves. Moreover, such a cleaning solution may not effectively kill some types of water born mold and/or bacteria, and therefore may inadequately sanitize the reservoir of a device. Other commonly recommended methods of cleaning a device with a reservoir include manual washing, scrubbing, and drying of the reservoir, which are often time consuming and considered to be undesirable to consumers.

Accordingly the inventors have identified that there is a continued interest in the development of novel devices, systems, and methods for sanitizing all or a portion of devices with reservoirs, including but not limited to the water reservoir of a device and any water therein.

BRIEF DESCRIPTION OF THE DRAWINGS

Reference is now made to the following detailed description which should be read in conjunction with the following figures, wherein like numerals represent like parts.

DETAILED DESCRIPTION

As explained in the background consumers may rarely clean devices with reservoirs. Bacteria, mold and other contaminants may therefore grow or otherwise accumulate within the reservoir. Although there are various known methods for cleaning reservoirs, such methods are often inconvenient, messy, time-consuming, etc., and therefore may be rarely performed. Such methods may also inadequately clean and/or sanitize the reservoir and any water therein. The inventors have therefore identified that there is a need in the art for technologies (e.g., devices, systems and methods) that enable convenient, easy and effective sanitization of reservoirs.

Aspects of the present disclosure relate to devices, systems and methods for sanitizing a reservoir of a device, such as a hot beverage maker, humidifier, animal watering machine, soda fountain, medical device or the like. The devices, systems and methods generally include a connector unit that is configured to couple to a port or other opening on the reservoir. The connector unit is configured to facilitate the provision of a sanitizing gas such as ozone into the reservoir, and the removal of the sanitizing gas from the reservoir. As will be described in detail later, the devices, systems and methods of the present disclosure are particularly useful for sanitizing a liquid reservoir of the above mentioned types of devices, as well as components that are in fluid communication with the liquid reservoir (e.g., a bottom tray, mist channels, etc.). It should be understood however that the technologies described herein are not limited to the specific applications described herein, and may be utilized to sanitize any type of reservoir.

Although the technologies described herein can be used with many sanitizing gases, the present disclosure focuses on the use of ozone as a sanitizing gas. This is because ozone ($O_3$) gas is an effective sanitizer, yet is relatively safe for consumer use. Indeed because of its strongly oxidizing properties, ozone can effectively kill or otherwise remove a wide range of organic and inorganic contaminants such as yeasts, bacteria, molds, viruses, other pathogens, and/or pollutants with which it comes into contact, e.g., via oxidation. Yet naturally over time and/or as it oxidizes contaminants, ozone may be chemically reduced to oxygen ($O_2$), which is safe for human consumption and for release into the environment. Ozone is also relatively easy to generate on site (and thus does not require the use of a storage tank), and leaves little or no chemical residue. For those and other reasons, ozone has been identified as a safe and effective sanitizing gas for use in the present disclosure. It should be understood, however, that the technologies described herein are not limited to the use of ozone, and may be employed with a wide variety of sanitizing gases.

As used herein, the term "fluidly coupled" means that two or more components are connected to one another such that a gas may be conveyed between them. In contrast, the term "coupled" when used alone means that two or more components are connected to one another chemically (e.g., via an adhesive), mechanically (e.g., via fasteners, mechanical interference, etc.), or by other means.

One aspect of the present disclosure relates to systems for sanitizing a reservoir, e.g., of a device. The systems described herein generally include a gas supply system, a connector unit configured to couple to a reservoir, and an exhaust system. More specifically, the connector unit is configured to be installed within an opening or "hole" in a portion of a reservoir, such as but not limited to a wall, cover, or bottom thereof. The opening in the reservoir may be part of a design of the reservoir (e.g., an inlet or outlet hole), or may be formed in the reservoir in another manner (e.g., by drilling, cutting, boring, etc. through a portion of the reservoir. In any case, the connector unit is configured such that it spans through a thickness of the portion of the reservoir when it is installed in the opening, with a proximal end of the connector unit disposed outside the reservoir, and a distal end of the connector unit inside the reservoir.

The gas supply system is configured to generate a sanitizing gas, such as but not limited to ozone. In addition, the gas supply system is configured to be fluidly coupled to the proximal end of the connector unit, e.g., directly or via a supply line. In either case, sanitizing gas generated by the gas supply system may be conveyed through an inlet passageway in the connector unit to an interior of the reservoir. In some instances, a first supply line may be used, and may have a proximal end coupled to the gas supply system and a distal end fluidly coupled to the proximal end of an inlet passageway in the connector unit. In such instances, sanitizing gas input into the first supply line from the gas supply system may be conveyed into a through the inlet passageway, and into the reservoir. In some instances, a second supply line may be used, and may have a proximal end that is fluidly coupled to the distal end of the inlet passageway. In such instances the distal end of the second supply line may be disposed within the reservoir, e.g., below a level of any liquid contained therein. In either case, sanitizing gas may be conveyed into the reservoir.

The exhaust system is generally configured to draw (e.g., excess) sanitizing gas out of the reservoir. In embodiments, the exhaust system is fluidly coupled to the reservoir (e.g., via the connector unit or another opening), and includes a pump that is configured to draw the sanitizing gas out of the reservoir and to a filter. When used, the filter may absorb or destroy the sanitizing gas or destroy it, e.g., by converting it to another composition. In instances where ozone is the sanitizing gas, for example, the filter may be configured to absorb ozone and/or convert it to oxygen. Non-limiting examples of suitable filters that may be used for that purpose include activated carbon filters and magnesium oxide filters. Put in other terms, the exhaust system may be disposed within or external to the reservoir, such that the sanitizing gas is not discharged into the environment.

Figure 1:
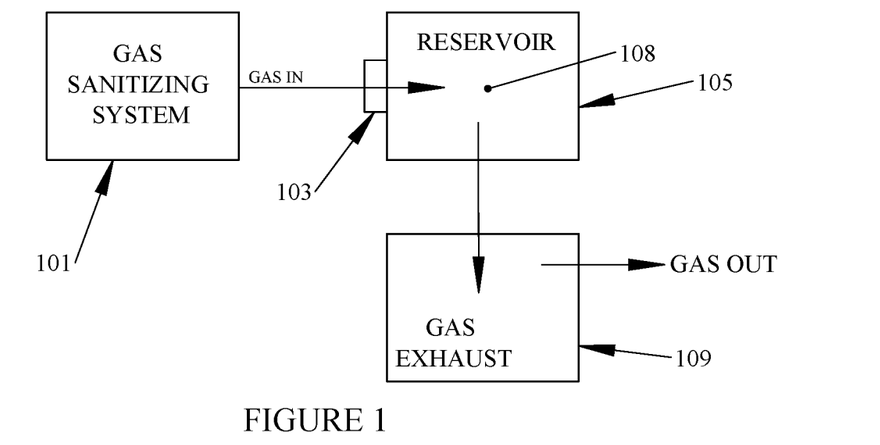
FIG. 1 is a block diagram illustrating sanitizing gas flow between a reservoir sanitizing system and a reservoir, consistent with the present disclosure.
Figure 1A:
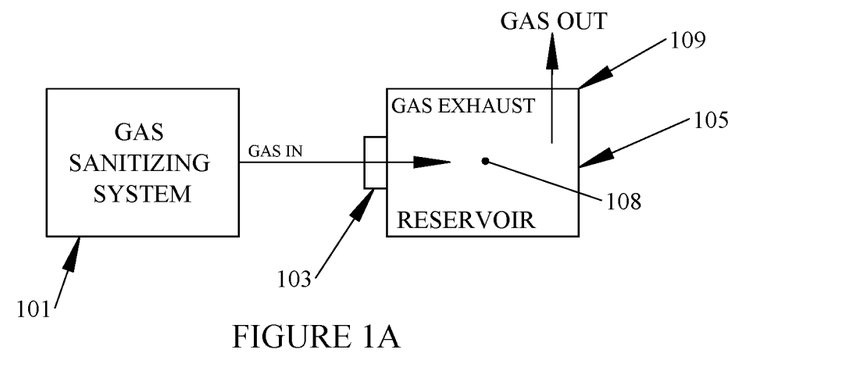
FIG. 1A is a block diagram illustrating sanitizing gas flow between a reservoir sanitizing system and a reservoir, consistent with the present disclosure.
Figure 1B:
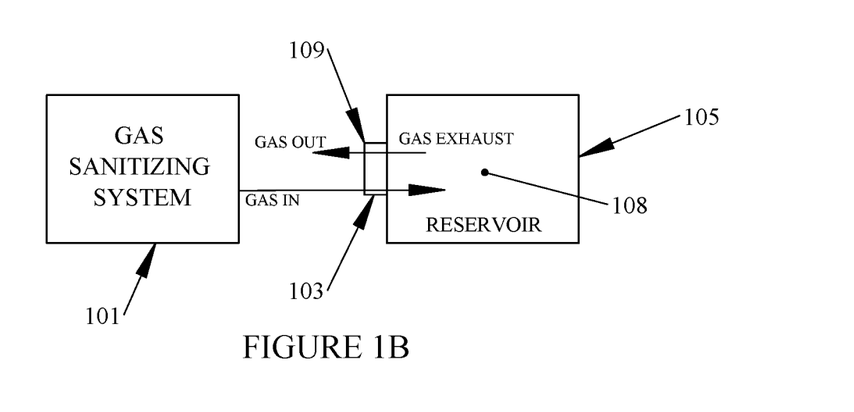
FIG. 1B is a block diagram illustrating sanitizing gas flow between a reservoir sanitizing system and a reservoir, consistent with the present disclosure.

FIGS. 1, 1A and 1B are block diagrams illustrating sanitizing gas flow between a reservoir sanitizing system and a reservoir, consistent with various embodiments of the present disclosure. As shown in each of FIGS. 1, 1A, and 1B, the reservoir 100 includes a sanitizing gas system 101 and a connector unit 103. The sanitizing gas system 101 is fluidly coupled to the connector unit 103 such that it can provide a gas inflow (gas in) to the connector unit 103. The connector unit 103 is fluidly coupled to a reservoir 105 including a liquid (e.g., water). As shown, the sanitizing gas system 101 may supply an inflow of sanitizing gas (Gas in) such as ozone to the connector unit 103. The inflow of sanitizing gas passes through the connector unit 103 into the reservoir 105. More particularly, in embodiments the inflow of sanitizing gas is conveyed from the connector unit 103 to beneath a surface of the liquid in the reservoir.

At least a portion of the sanitizing gas supplied by the gas inflow may sanitize the liquid in the reservoir (if any), as well as portions of the reservoir that are below the level of the liquid (if any). In addition, at least a portion of the sanitizing gas supplied by the gas inflow may evolve from the liquid into the air 108 within the reservoir 105 and sanitize the portion of the reservoir 105 that is above the level of the liquid. Excess sanitizing gas within the reservoir 105 may be converted to another composition and/or be removed from the interior of the reservoir 105 via a gas outflow (gas out).

In that regard, FIGS. 1, 1A, and 1B primarily differ in the manner in which an exhaust system 109 is implemented for safe removal of the sanitizing gas. As shown in such FIGS., the exhaust system 109 may: be or include a filter that is located within the reservoir 105 (as shown in FIG. 1); be external to the reservoir such that the gas continues to migrate in an enclosed environment until it reaches the exhaust system (as shown in FIG. 1A); or may be integrated into the connector unit 103 (as shown in FIG. 1B). In embodiments, the exhaust system 109 may be configured to remove the sanitizing gas and/or convert the excess sanitizing gas to another composition, as discussed previously.

Figure 2:
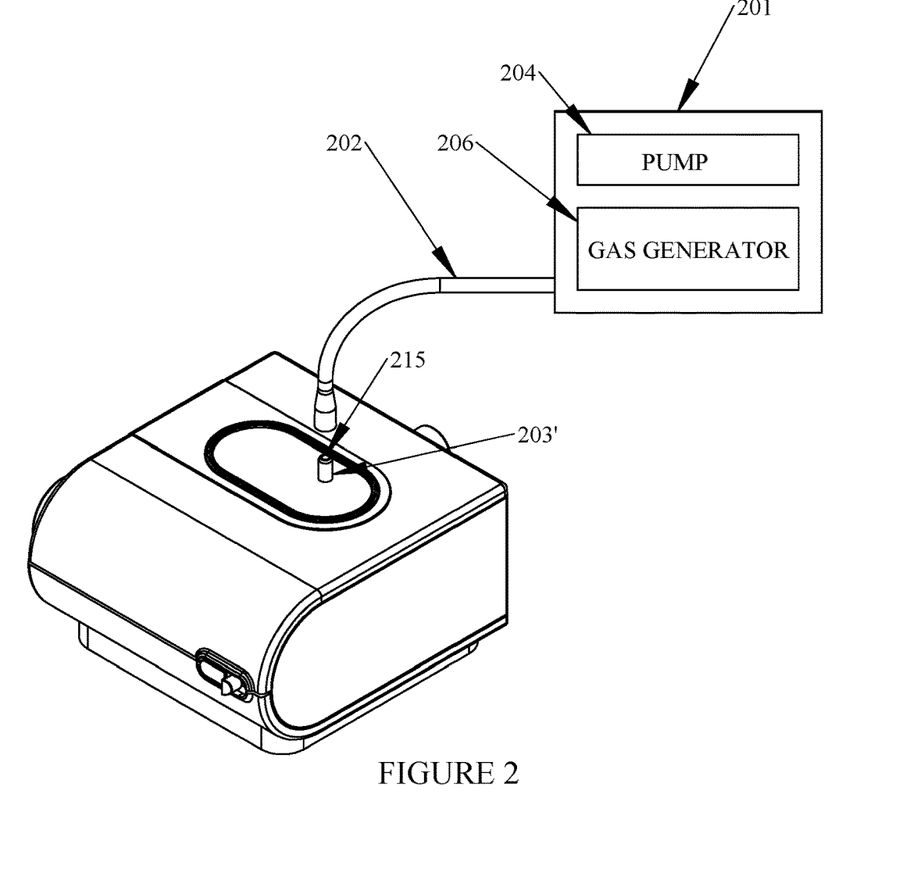
FIG. 2 is a block diagram of another example of a reservoir sanitizing system consistent with the present disclosure.
Figure 2A:
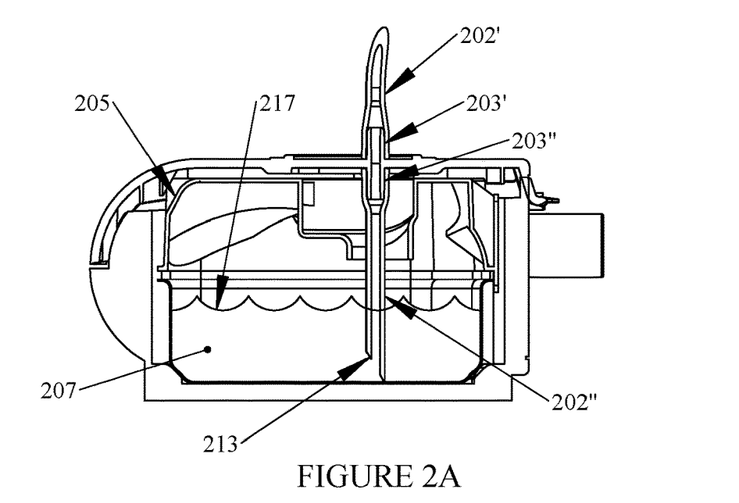
FIG. 2A is a cross-sectional view of a portion of a reservoir sanitizing system consistent with the present disclosure, as installed in a reservoir.

FIGS. 2 and 2A are block diagrams of one example of a reservoir sanitizing system consistent with the present disclosure. As shown, the reservoir sanitizing system includes a sanitizing gas system 201 that is fluidly coupled to a connector unit 203 having a proximal end 203'. In this embodiment, the sanitizing gas system 201 includes a gas supply including a pump 204 and a gas generator 206. The gas generator 206 is configured to generate a sanitizing gas, such as ozone or another sanitizing gas. The pump 204 (e.g., an air pump) is configured to generate a flow of air to convey the air to the ozone generator 206 and then sanitizing gas to a proximal end of a first supply line 202. The distal end of the first supply line 202 is coupled to the proximal end 203' of the connector unit.

The connector unit 203 includes an inlet passageway and is generally configured to be installed or pre-formed within a portion of a reservoir 205, such as but not limited to a wall, bottom, top, or cover of a reservoir. When so installed, the connector unit 203 spans through a thickness of a portion of reservoir 205, such that the proximal end 203' is exterior to the reservoir 205 and the distal end 203" of the connector unit 203 is inside the reservoir 205, as best shown in FIG. 2A. A second supply line 202' is fluidly coupled to the proximal end 203' of the connector unit 203, as also shown in FIG. 2A. The second supply line 202' is configured to convey a sanitizing gas supplied through the inlet passageway of the connector unit 203 to the interior of the reservoir 205, e.g., below the surface of any liquid (e.g., water) 207 therein.

As discussed above, in the embodiment of FIGS. 2 and 2A the sanitizing gas system 201 (and, more particularly, the gas generator 206) is fluidly coupled to the interior of reservoir 205 by the first supply line 202, the connector unit 203, and the second supply line 202'. In other embodiments the inlet passageway of the connector unit 203 may be configured such that a single supply line may be passed there through. In such embodiments, the proximal end of the supply line may be coupled to the gas generator 206, an intermediate portion of the supply line may pass through the inlet passageway in the connector unit 203, and a distal end of the supply line may be disposed inside the reservoir 205, e.g., below a surface 217 of any liquid 207 therein.

Figure 3:
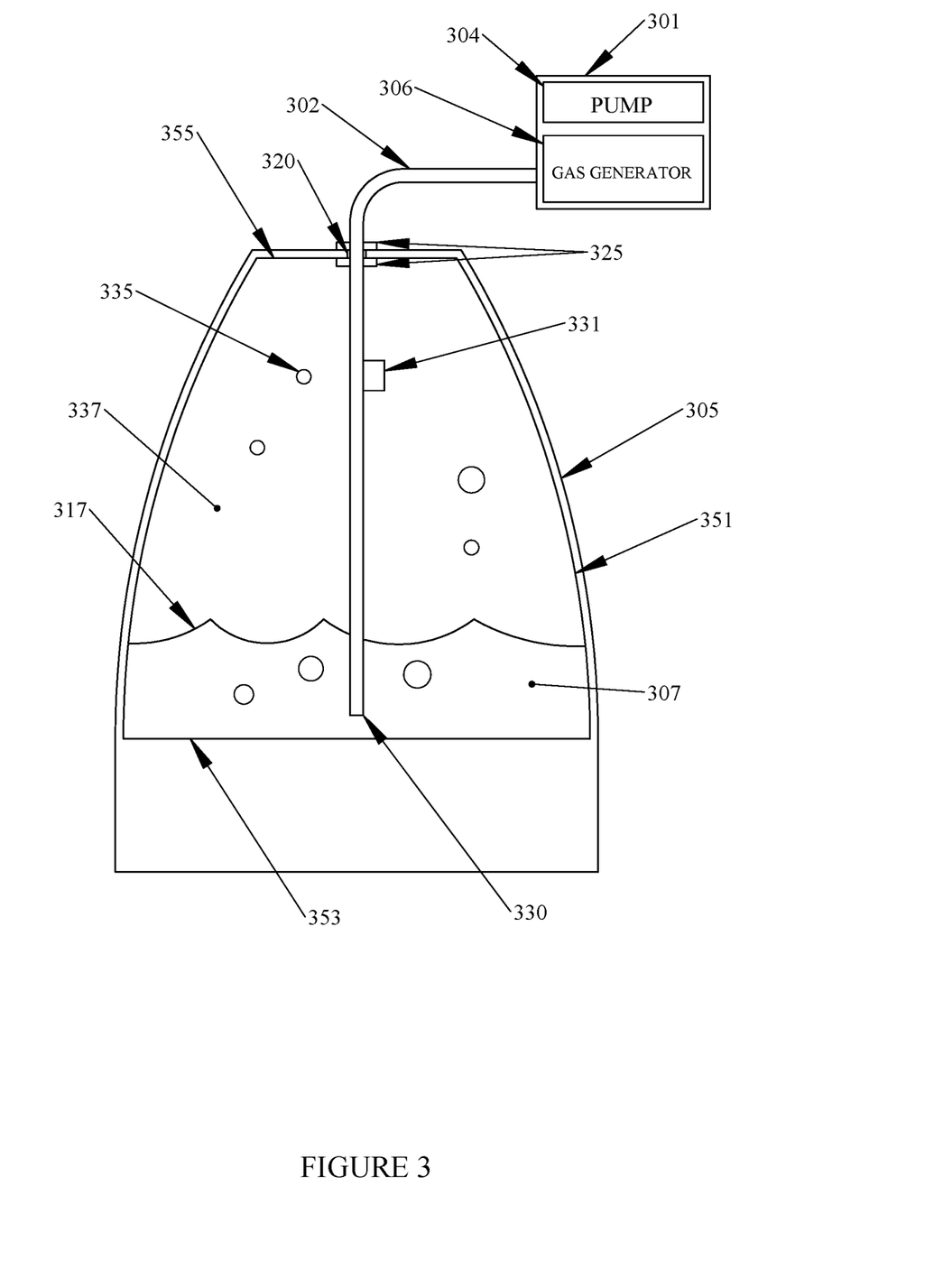
FIG. 3 is a general diagram showing another example of a gas sanitizing system consistent with the present disclosure, fluidly coupled to a reservoir.

That concept is shown in FIG. 3, which depicts another example of a reservoir sanitizing system consistent with the present disclosure. As shown in FIG. 3 a single supply line 302 may be used to supply a sanitizing gas 335 into a reservoir 305 (instead of a first and second supply lines 202, 202' as shown in FIGS. 2 and 2A). Moreover in this embodiment, the connector unit includes or is in the form of a sealing element 325 that is configured to couple to an inward facing surface of a hole 320 in a wall, top, or bottom of a reservoir 305. The sealing element may be in the form of a grommet or other suitable sealing element. In the embodiment of FIG. 3, the sealing element 325 is a grommet having a first sealing portion 325' that is disposed exterior to the reservoir 305 and second sealing portion 325" that is disposed internal to the reservoir 305. In embodiments, the sealing element 325 is configured such that a water and/or gas tight seal is present between the sealing element 325 and the inward facing surface of hole 320. The sealing element may also have a hole or passage there through, which may be configured to allow a distribution line to be passed there through, as shown in FIG. 3.

As shown in FIG. 3, the reservoir sanitizing system includes a supply line 302. The supply line 302 is configured to be inserted through the hole 320 such that a distal end thereof is located within the reservoir 305, e.g., below a surface of any liquid 307 (e.g. water) therein. The proximal end of the supply line 302 is fluidly connected to a gas sanitization system 301 (and, more particularly to gas generator 306). The gas sanitization system 301 includes a pump 304 (e.g., an air pump) fluidly coupled to a gas generator 306. In operation, the gas generator 306 may generate a sanitizing gas 335 which may be conveyed into supply line 302 via a flow of air generated by the pump 304. The sanitizing gas 335 may be conveyed through the supply line 302 into the reservoir 305.

An optional check valve 331 may be provided on a distal portion of supply line 302. When used, the optional check valve is generally configured to prevent a backflow of liquid 307 into the supply line 302. An optional sensor (not shown) may also be provided to sense a presence and/or concentration of sanitizing gas (e.g. ozone gas) within the interior of reservoir 305 and/or within supply line 302. In some embodiments the sensor (when used) may be configured to provide a signal to a user interface, wherein the signal causes the user interface to indicate whether or not a safe level of the sanitizing gas is present in the reservoir 305, and/or to indicate when the reservoir is safe to use.

The sanitizing gas system 301 further includes an exhaust system (not separately shown), which is fluidly coupled to the reservoir. The exhaust system may include a removable filter coupled to the reservoir 305 that may work to absorb or convert the excess sanitizing gas to another composition, such an activated carbon filter. In embodiments the exhaust system may be configured as a removable part of the connector unit 325, such that supply line 302 may still pass through the connector unit 325 and excess gas in the reservoir 305 may be exhausted through an outlet passageway in the connector unit 325. In other embodiments the exhaust system may be external to the reservoir 305, and may be fluidly coupled to the reservoir in another manner (e.g., via a second hole in the reservoir, an outlet line, etc.). In either case the exhaust system may include a pump (e.g., a vacuum pump) to draw sanitizing gas out of the reservoir 305, and a filter to absorb and/or convert sanitizing gas to another composition, as previously described.

When the distal end 330 of the supply line 302' is disposed beneath a surface 317 of a liquid 307 within the reservoir 305, the sanitizing gas 335 may be introduced into the liquid 107. In such instances a portion of the sanitizing gas 335 may sanitize the liquid 307 and the portions of the reservoir 305 that are below surface 317. In addition, at least a portion of the sanitizing gas 335 may evolve from the liquid 307 into the air 337 within the reservoir 305, whereupon the sanitizing gas 335 may sanitize the air 337 and the interior surfaces of the walls 351 and cover 355. Likewise in instances where the distal end 330 is be disposed above surface 317, and/or no liquid 307 may be present within reservoir 305, the sanitizing gas 335 may sanitizing the air 337 and exposed surfaces of the walls 351, cover 355, and bottom 353.

During the sanitization of reservoir 305, all or a portion of the sanitizing gas 335 may be converted to another composition. For example in instances where the sanitizing gas is ozone, all or a portion of the ozone may be converted to oxygen during the sanitization of the reservoir 305. However, excess sanitizing gas 335 may be present within the air 337, and may need to be removed or exhausted in order for the reservoir to be safely used. A filter may be configured to remove all or a portion of the sanitizing gas 335 conveyed thereto. For example, a filter may be configured to absorb at least a portion of the sanitizing gas 335. Alternatively or additionally, the filter may be configured to convert the sanitizing gas to another composition, such as a composition that is acceptable for human inhalation and/or exhaust into the environment. In instances where the sanitizing gas 335 is ozone, for example, the filter may be configured to convert all or a portion of the sanitizing gas to oxygen. Non-limiting examples of suitable filters that may be used as filter for converting ozone to oxygen include activated carbon filters, magnesium oxide filters, combinations thereof, and the like.

For the sake of clarity and ease of understanding, it is noted that FIG. 3 depicts a reservoir 305 in combination with the reservoir sanitizing system 301, but it should be understood that the reservoir sanitizing systems described herein need not include the reservoir. Indeed, the systems described herein may be used with any suitable reservoir, and are not limited to use with reservoirs consistent with those illustrated in the figures.

Another aspect of the present disclosure relates to methods for sanitizing a reservoir. In that regard reference is made to FIG. 4, which is a flow chart of example operations of one example of a reservoir sanitization method consistent with the present disclosure. As shown, the method 400 begins at block 401. The method may then advance to optional block 403, pursuant to which reservoir sanitizing system with the present disclosure may be installed through a connector unit or a hole in a reservoir, such that the distal end of the supply line traverses the wall of the reservoir and the proximal end of the supply line is fluidly coupled to the a gas generator.

Figure 4:
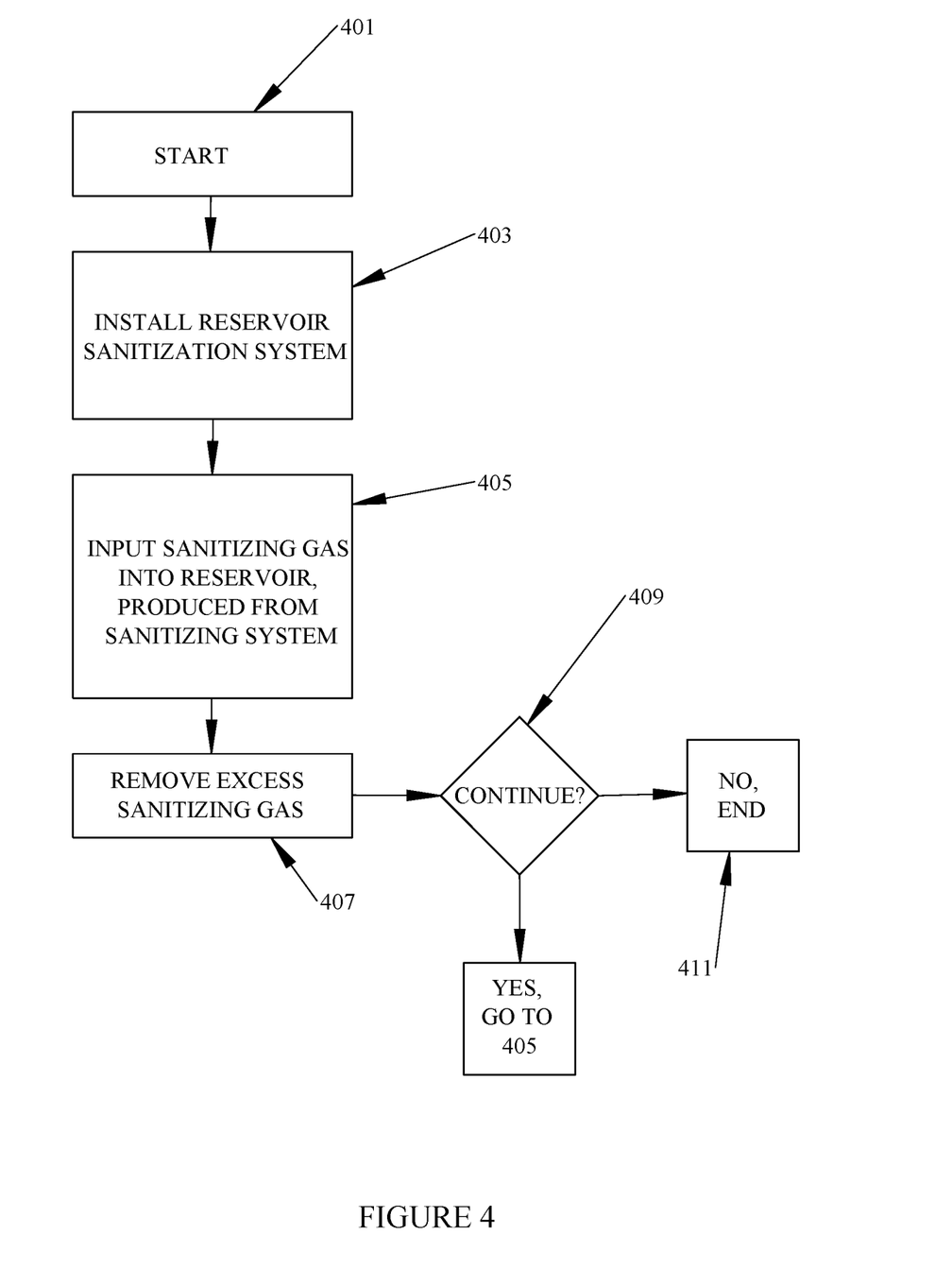
FIG. 4 is a flow chart of example operations of an example reservoir sanitization method consistent with the present disclosure.

Following the operations of block 403 or if block 403 is omitted (e.g. where a reservoir sanitizing system is embedded in a cover), the method may proceed to block 405. Pursuant to block 405 a sanitizing gas may be provided into a reservoir via a supply line e.g., as described above. Thus for example, operations pursuant to block 405 may include generating a sanitizing gas with a gas generator, causing the sanitizing gas to flow into a supply line, and into the reservoir, as previously described. At least a portion of the sanitizing gas so provided may sanitize the interior of the reservoir, including any liquid (e.g., water therein).

The method may then advance to block 407, pursuant to which excess sanitizing gas may be removed from the interior of the reservoir. Consistent with the foregoing description, operations pursuant to block 407 may include drawing sanitizing gas from the interior of the reservoir into an exhaust system. The operations pursuant to block 407 may also include conveying the sanitizing gas to a filter, as discussed above.

Following the operations of block 407 the method may proceed to block 409, pursuant to which a decision may be made as to whether the method is to continue. The outcome of the decision block 409 may be contingent on a sensor signal provided, e.g., by an optional sensor or on some other criteria. In any case if the method is to continue it may loop back to block 405, but if not, the method may proceed to block 411 and end.

The following examples pertain to additional non-limiting embodiments of the present disclosure.

EXAMPLES

Example 1

According to this example there is provided a system for sanitizing a device with a reservoir, including: a gas supply system including a pump and a gas generator, the gas supply system configured to supply a sanitizing gas; a connector unit including an inlet passageway, the inlet passageway including a proximal end and a distal end; a first supply line having a proximal and a distal end, wherein the proximal end of the first supply line is fluidly coupled to the gas supply system and the distal end of the first supply line is fluidly coupled to the proximal end of the inlet passageway; a second supply line including a proximal end and a distal end, wherein the proximal end of the second supply line is coupled to the distal end of the inlet passageway; and an exhaust system configured to remove the sanitizing gas; wherein the connector unit is configured to span a thickness of a portion of a reservoir when it is installed into the portion, such that the proximal end of the inlet passageway is external to the reservoir and the distal end of the inlet passageway is inside the reservoir.

Example 2

This example includes any or all of the features of example 1, wherein the exhaust system includes a removable activated carbon filter.

Example 3

This example includes any or all of the features of example 1, and further includes a check valve coupled to the second supply line.

Example 4

This example includes any or all of the features of example 1 and further includes a sensor for sensing sanitization gas in the reservoir.

Example 5

This example includes any or all of the features of example 1, wherein the sanitizing gas is ozone gas.

Example 6

According to this example there is provided a system for sanitizing a device with a reservoir with a water reservoir comprising: a gas supply system including a pump and a gas generator, the gas supply system configured to supply a sanitizing gas; a sealing element configured to form a water-tight seal with an opening in the reservoir, the sealing element having an opening there through; a supply line having a proximal end and a distal end, wherein the proximal end is fluidly coupled to the gas supply system, an intermediate portion of the supply line is configured to extend through the opening in the sealing element such that the distal end of the supply line is disposed within the reservoir when the sealing element is installed within the opening; and an exhaust system configured to remove the sanitizing gas.

Example 7

This example includes any or all of the features of example 6, wherein the exhaust system includes a removable filter.

Example 8

This example includes any or all of the features of example 7, wherein the removable filter is a removable activated carbon filter or a removable magnesium oxide filter.

Example 9

This example includes any or all of the features of example 6, and further includes a check valve coupled to between the distal end and the intermediate portion of the supply line.

Example 10

This example includes any or all of the features of example 6, and further includes a sensor for sensing sanitization gas in the reservoir.

Example 11

This example includes any or all of the features of example 6, wherein the sanitizing gas is ozone gas.

Example 12

According to this example there is provided a method for sanitizing a reservoir, comprising: installing a connector unit into a hole in a portion of a reservoir, the connector unit including an inlet passageway including a proximal end and a distal end; fluidly coupling the proximal end of the inlet passageway to a gas supply system configured to supply a sanitizing gas; causing a sanitizing gas to flow into the reservoir via the connector unit; and exhausting the sanitizing gas from the reservoir.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A system for sanitizing comprising:
   a reservoir configured to be coupled to a continuous positive airway pressure device;
   a gas supply system configured to supply a sanitizing gas;
   a cover to extend across an opening on a top surface above a water level of the reservoir of the continuous positive airway pressure device, the cover comprising a connector unit comprising an inlet passageway, the inlet passageway comprising a proximal end and a distal end, wherein the connector unit spans a thickness of a portion of the said cover such that when the cover is installed in the reservoir, the inlet passageway extends substantially vertically, the proximal end is located on an outward facing side of said cover above the water level within the reservoir, and the distal end of the inlet passageway faces an interior of the reservoir;
   a first supply line configured to be fluidly coupled to the gas supply system and fluidly coupled to the proximal end of the inlet passageway.

2. The system of claim 1, further comprising a second supply line configured to be fluidly coupled to the distal end of the inlet passageway.

3. The system of claim 1, further comprising an exhaust system configured to remove the sanitizing gas.

4. The system of claim 3, wherein the exhaust system comprises a removable activated carbon filter.

5. The system of claim 2, further comprising a check valve coupled to the second supply line.

6. The system of claim 1, wherein the sanitizing gas is ozone gas.

7. The system of claim 1, wherein the connector unit is pre-formed in the cover.

8. The system of claim 2, wherein the connector unit is pre-formed in the cover.

9. A system for sanitizing comprising:
   a reservoir configured to be coupled to a continuous positive airway pressure device;
   a cover to extend across an opening on a top surface above a water level of the reservoir of the continuous positive airway pressure device, the cover comprising a connector unit comprising an inlet passageway comprising a proximal end and a distal end;
   wherein;
   the inlet passageway spans a thickness of the cover, such that when the cover is installed across the opening of the reservoir, the inlet passageway extends substantially vertically and the proximal end of inlet passageway is located on an outward facing side of said cover above the water level within the reservoir and the distal end of the inlet passageway is located on an inward facing side of said cover; and
   the proximal end of the inlet passageway is configured to fluidly couple to a first supply line to receive a flow of sanitizing gas.

10. The system of claim 9, wherein the distal end of the inlet passageway is configured to fluidly couple to a second supply line to convey sanitizing gas to within said reservoir.

11. The system of claim 9, wherein the connector unit is pre-formed in said cover.

12. A continuous positive airway pressure (CPAP) sanitizing system comprising:
    a continuous positive airway pressure (CPAP) reservoir configured to be coupled to a continuous positive airway pressure (CPAP) device;
    a top cover configured to be coupled to an opening of the CPAP reservoir above a liquid level, the top cover including a connector unit with an inlet passageway having a proximal end and a distal end,
    wherein the proximal end is configured to be fluidly coupled with a supply line to supply a sanitizing gas to the CPAP reservoir and the distal end is configured to be above the liquid level of the CPAP reservoir.

13. A continuous positive airway pressure (CPAP) sanitizing system comprising:
    a continuous positive airway pressure (CPAP) reservoir configured to be coupled to a continuous positive airway pressure (CPAP) device;
    a top cover configured to be coupled to an opening of the CPAP reservoir above a liquid level, the top cover comprising a connector unit including an inlet passageway having a proximal end and a distal end;
    wherein when the top cover is coupled to the CPAP reservoir, the distal end is within the CPAP reservoir above the liquid level of the CPAP reservoir and the proximal end is configured to fluidly couple to a supply line to receive a flow of sanitizing gas.

* * * * *